United States Patent [19]

Myers, Jr. et al.

[11] 4,098,835
[45] Jul. 4, 1978

[54] VINYL NORTRICYCLANE

[75] Inventors: Harry K. Myers, Jr., Aston; James E. Lyons, Wallingford; Abraham Schneider, Overbrook Hills, all of Pa.

[73] Assignee: Sun Oil Company of Pennsylvania, Philadelphia, Pa.

[21] Appl. No.: 829,301

[22] Filed: Aug. 31, 1977

[51] Int. Cl.$^2$ .............................................. C07C 15/00
[52] U.S. Cl. ........................ 260/666 PY; 260/666 B; 44/80; 149/109.4; 149/109.6
[58] Field of Search ............. 260/666 PY; 149/109.4, 149/109.6

[56] References Cited
U.S. PATENT DOCUMENTS 3,978,147  8/1976  Wilke et al. .................. 260/666 PY

OTHER PUBLICATIONS

Boris Bogdanovic, Angew. Chem. Intern. Ed., vol. 12, No. 12, pp. 954–964, 1973.

*Primary Examiner*—Veronica O'Keefe
*Attorney, Agent, or Firm*—J. Edward Hess; Donald R. Johnson; Anthony Potts, Jr.

[57] ABSTRACT

Processes for preparing vinyl nortricyclane (I) and its hydrogenated derivative, ethyl nortricyclane (II) are disclosed. The nortricyclane (II) can be used as a high energy fuel or a fuel diluent. Process involves codimerization of norbornadiene and ethylene in the presence of a homogeneous catalytic system of cobaltic or cobaltous acetylacetonate, 1,2-bisdiphenylphosphino ethane and an alkyl aluminum chloride to yield the vinyl nortricyclane (I). The latter can be hydrogenated to ethylnortricyclane.

12 Claims, No Drawings

VINYL NORTRICYCLANE

BACKGROUND OF THE INVENTION

The invention herein described was made in the course of or under a contract thereunder with the United States Air Force Systems Command.

The invention relates to the catalytic codimerization of norbornadiene and ethylene. Particularly the invention relates to the preparation of an olefinic codimer of norbornadiene and ethylene using a specified catalyst system. Hydrogenation of the olefinic codimer yields a saturated codimer having utility as a high energy fuel or as a diluent for such fuels. The ethylene is referred to hereinafter as E.

High energy fuel, which is often referred to as a high density fuel, can be used in either jet or rocket propulsion. Jet propulsion includes a jet engine, which can be used for a missile plane and others and includes the three basic types, i.e., ramjet, turbo-jet and pulse jet. The term rocket generally refers to a device containing its own oxygen or oxidizing agent.

Norbornadiene (III) is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

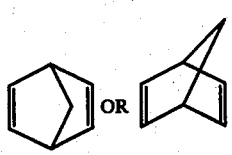

NBD can be easily dimerized to an exo-exo hexacyclic dimer. Thus one problem in reacting NBD with another hydrocarbon reactant is to minimize the formation of the foregoing dimer while encouraging the formation of the desired codimer.

In an article by Borislav Bogdanovic in Angew.-Chem. internat. Edit./Vol. 12(1973) No. 12, page 954 and ff. the reaction of norbornadiene and ethylene in the presence of a catalyst system, and the resulting products are disclosed. The reaction yields 5-vinylnorbornene, and its hydrogenation to 5-ethylnorbornane is disclosed. The system is different then those disclosed herein. The article is titled "Asymmetric Synthesis with the Aid of Homogeneous Transition-Metal Catalyst."

SUMMARY OF THE INVENTION

NBD and E are codimerized to the codimer vinyl nortricyclane (I). Hydrogenation of the latter yields a hydrogenated product II, having utility as a high density fuel or a diluent for such a fuel. The codimerization involves contacting NBD and E in the presence of a catalytic amount of a catalytic system of cobaltic or cobaltous acetylacetonate, 1,2-bisdiphenylphosphino ethane and one of three alkyl aluminum chlorides. The structure of codimer vinyl nortricyclane (I) and the hydrogenated product, ethyl nortricyclane (II), are as follows:

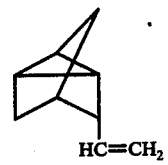

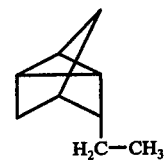

DESCRIPTION

Cobaltic acetylacetonate (Co(C$_5$H$_7$O$_2$)$_3$) is referred to hereinafter as CoA$_3$ whereas the cobaltous form (Co(C$_5$H$_7$O$_2$)$_2$) is referred to as CoA$_2$. Collectively the two are referred to as CoA. The 1,2-bisdiphenylphosphino ethane is referred to as DIPHOS while the alkyl aluminum chloride is referred to as AAC.

The catalytic codimerization of NBD and E via present invention can be represented by the following formula reaction:

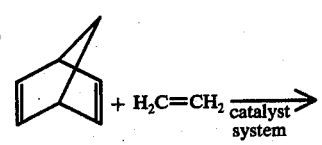

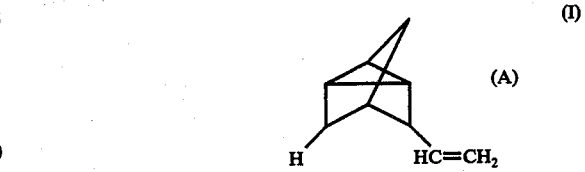

As shown NBD and E are contacted in the presence of a catalytic amount of the catalyst system defined herein. Coproducts may also be formed.

Vinyl nortricyclane (I), at 97% purity, has a net heat of combustion of 143, 504 BTU/gallon, a density at d20/4 of 0.9203, and a KV at 100° F of 1.04 cs. It has 3 rings, its formula is C9H$_{12}$ and has a C/H molar ratio of 0.750.

Vinyl nortricyclane (I) can be hydrogenated to ethyl nortricyclane (II). The hydrogenation can occur in the presence of a suitable hydrogenation catalyst such as PtO$_2$. The temperature of hydrogenation can range from ambient to 100°–200° C.

The NBD used can contain a nominal amount of similar hydrocarbons, however, which if present should not be of a type which could adversely affect the reaction. If the NBD used contains undesirable hydrocarbons, they can be removed by known means. The foregoing also applies to the E used. Thus the hydrocarbons used in the invention can consist essentially of NBD and E.

In the codimerization of NBD and E one mole of each reacts with the other to form one mole of vinyl nortricyclane (I). However, if the NBD to E mole ratio is too large, homodimerization can occur with an adverse effect on codimer yields. On the other hand, if the NBD to E mole ratio is too low then the yield per pass can be too low and hence uneconomical. Within the aforementioned range a preferred NBD to E mole ratio is in the range between from about 0.01 to about 500 with about 0.1 to about 50 more preferred.

The catalytic system favoring the aforementioned codimerization reaction A contains three components. All three components of the catalyst system are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to AS DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system. Thus the catalyst system can consist of the aforementioned components.

The codimerization of NBD and E with the catalyst system can occur at ambient temperature. Thus the temperature of the homogeneous feed catalyst system mixture need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally, however, the codimerization of NBD and E with a reasonable amount of the catalyst system is not characterized by an extremely rapid exotherm.

Selective codimerization of the NBD and E most efficiently occurs in a liquid phase and therefore it is not desirable to have the reaction temperature largely exceed the boiling points of the NBD and/or any solvent. Conversely, if the temperature is too low the reaction rate can be too slow to be economically feasible. An operable temperature range is between from about $-20°$ to about $100°$ C with about $25°$ to about $85°$ C a preferred range. The operating pressure can vary substantially, however, it can range from about atmospheric up to about 2000 psi with about 1000 psi a preferred upper value. Process economics favor lower operating pressure, however, a moderately elevated reaction pressure may be desirable to keep the E in solution.

The reaction time required for an economically satisfactory selectivity and/or yield depends on a number of factors, such as catalyst to feed ratio, as well as operating conditions. Also, the economics depend on capital investment versus conversion per pass and the like. The catalyst to feed ratios are discussed hereinafter while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, diethylether, chlorobenzene, bromobenzene, chlorinated cyclohexane and the like. As to the amount of solvent used, excessive amounts decrease the reaction rate, and thus adversely affect the economics for a commercial operation.

The amount of CoA present should be catalytically sufficient to obtain the desired product. Generally the NBD to CoA mole ratio can range between from about 10 to about 2000 with a preferred range between from about 20 to about 1000.

Another component of the catalyst system is DIPHOS which has the following formula: $[(C_6H_5)_2PCH_2]_2$. The amount of this second component of the catalyst system should be catalytically sufficient to obtain the desired product. Generally the DIPHOS to CoA mole ratio can range between from about 0.1 to about 5 with a preferred range between from about 1 to about 4.

DEAC, EADC or EASC is another component of the catalyst system with DEAC preferred. The amount of the third component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

To further illustrate the invention, the following examples and comparative runs are provided.

EXAMPLES

The codimerization of the NBD and E was carried out in the following manner. In a Fisher-Porter glass pressure vessel were mixed 0.356 grams (1.0 millimole) of $CoA_3$, 0.597 grams (1.5 millimole) of DIPHOS, and 15 milliliters of toluene all at a temperature of $24°$ C and the resulting mixture was deaerated. In a second pressure vessel were mixed 10 milliliters of toluene, 10.5 grams (115 millimoles) of NBD all at a temperature of $24°$ C and the resulting mixture was deaerated. In a third pressure vessel 9.67 grams (345 millimoles) of E were condensed at $-104°$ C. Then the contents of the second vessel were chilled to $-104°$ C and the condensed E was distilled into it. Then the contents of the first vessel were chilled to $-104°$ C and ¼ of the volume of the second vessel was pumped into it. To the first vessel 15 milliliters of a 1 molar solution of DEAC in toluene were added and occasionally the vessel was vented. Afterwards the remainder of the second vessel were slowly introduced into the first vessel while its contents were allowed to warm, occasionally using a 55° C oil bath, to 54° C over a 150 minute period. At the end of the aforementioned period the pressure was allowed to reach 75 psig. The temperature rose to a maximum of 59° C after 160 minutes and then fell to 50° C where it remained until 300 minutes had elapsed. At the end of the 300 minutes the entire remaining mixture was quenched with aqueous HCl to kill the catalyst. Product analysis via vapor phase chromatography (v.p.c.), of quenched aliquots were obtained at various intervals and are summarized in the table below.

TABLE

| Time,min. | T,° C | % Yield | | |
|---|---|---|---|---|
| | | Total-Codimer | Vinyl Nortricyclane | NBD Binor |
| 160 | 59 | 15 | 14 | 0.5 |
| 210 | 51 | 21 | 19 | 0.5 |
| 300 | 50 | 20 | 17 | 0.6 |

The foregoing yields indicate that the exothermic reaction was over at about 200 minutes. Reaction to the vinyl nortricyclane (I) was highly selective, i.e. about 90% selectivity.

The resulting reaction mixture was purified by preparative scale gas chromatography. The structure of the 97% pure material was determined by mass spectrometry, infrared analysis and nuclear magnetic resonance spectroscopy.

Similar results will be obtained if $CoA_2$ replaces $CoA_3$ in reaction A and/or the DEAC is replaced by EADC or EASC.

The vinyl nortricyclane (I) can be hydrogenated with hydrogen using any one of numerous hydrogenation catalysts such as $PtO_2$. The hydrogenation will proceed rapidly to the ethyl nortricyclane (II).

The NBD-E codimerization reaction was attempted using phosphine complexes of Pd, Rh and Fe in lieu of the $CoA_3$ heretofore described. None of these complexes appeared to have led to the formation of vinyl nortricyclane.

The invention claimed is:

1. Process for the catalytic codimerization of norbornadiene and ethylene comprising:
   (a) contacting norbornadiene and ethylene in the presence of a catalytic amount of a homogeneous catalytic system of cobaltic or cobaltous acetylacetonate, 1,2-bisdiphenylphosphino ethane and one of the following alkyl aluminum chlorides: diethylaluminum chloride, ethyl aluminum dichloride and ethyl aluminum sesquichloride;
   (b) having the contacting occurring at a temperature within the range from between about −20° to about 100° C; and
   (c) continuing the contacting until vinyl nortricyclane is prepared.

2. Process according to claim 1 wherein the mole ratio of the bisdiphenylphosphino ethane to cobaltic acetylacetonate is in the range between from about 0.1 to about 5.

3. Process according to claim 1 wherein the mole ratio of norbornadiene to ethylene is in the range between from about 0.01 to about 500.

4. Process according to claim 1 wherein the mole ratio of the alkyl aluminum chloride to the acetylacetonate is in the range between from about 0.5 to about 100.

5. Process according to claim 1 wherein the mole ratio of the norbornadiene to the acetylacetonate mole ratio is in the range between from about 10 to about 2000.

6. Process according to claim 1 wherein an inert solvent is present.

7. Process according to claim 6 wherein the inert solvent is selected from the group consisting of aromatic hydrocarbon, cycloparaffin, ether, halogenated aromatic hydrocarbon, halogenated paraffin and halogenated cycloparaffin.

8. Process according to claim 7 wherein the mole ratio of the bisdiphenylphosphino ethane to the acetylacetonate is in the range between from about 0.1 to about 5.

9. Process according to claim 8 wherein the mole ratio of norbornadiene to ethylene is in the range between from about 0.01 to about 500.

10. Process according to claim 9 wherein the mole ratio of the alkyl aluminum chloride to the acetylacetonate is in the range between from about 0.5 to about 100.

11. Process according to claim 10 wherein the mole ratio of the norbornadiene to the acetylacetonate mole ratio is in the range between from about 10 to about 2000.

12. Process according to claim 11 wherein the temperature range is between from about 25° to about 85° C and the mole ratio of norbornadiene to ethylene is in the range between from about 0.01 to about 50.

* * * * *